United States Patent
Oda et al.

(10) Patent No.: US 11,739,280 B2
(45) Date of Patent: *Aug. 29, 2023

(54) LUBRICANT ADDITIVE, LUBRICANT ADDITIVE COMPOSITION, AND LUBRICATING OIL COMPOSITION CONTAINING THE SAME

(71) Applicant: NOF CORPORATION, Tokyo (JP)

(72) Inventors: Kazuhiro Oda, Amagasaki (JP);
Yutaro Shimizu, Amagasaki (JP);
Hideki Kawamoto, Amagasaki (JP)

(73) Assignee: NOF CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/439,087

(22) PCT Filed: Mar. 10, 2020

(86) PCT No.: PCT/JP2020/010345
§ 371 (c)(1),
(2) Date: Sep. 14, 2021

(87) PCT Pub. No.: WO2020/184570
PCT Pub. Date: Sep. 17, 2020

(65) Prior Publication Data
US 2022/0154094 A1 May 19, 2022

(30) Foreign Application Priority Data

Mar. 14, 2019 (JP) ................................. 2019-047823
Feb. 20, 2020 (JP) ................................. 2020-027132

(51) Int. Cl.
*C10M 129/68* (2006.01)
*C10M 133/06* (2006.01)
*C10M 137/10* (2006.01)
*C10M 169/04* (2006.01)
*C10N 30/00* (2006.01)
*C10N 10/04* (2006.01)
*C10N 30/06* (2006.01)
*C10N 30/12* (2006.01)
*C10N 40/08* (2006.01)
*C10N 40/20* (2006.01)
*C10N 40/25* (2006.01)

(52) U.S. Cl.
CPC ........ *C10M 129/68* (2013.01); *C10M 133/06* (2013.01); *C10M 137/10* (2013.01); *C10M 169/04* (2013.01); *C10M 2207/28* (2013.01); *C10M 2215/04* (2013.01); *C10M 2223/045* (2013.01); *C10N 2010/04* (2013.01); *C10N 2030/06* (2013.01); *C10N 2030/12* (2013.01); *C10N 2030/45* (2020.05); *C10N 2040/08* (2013.01); *C10N 2040/20* (2013.01); *C10N 2040/25* (2013.01)

(58) Field of Classification Search
CPC ........ C10M 2207/28; C10M 2207/289; C10M 2209/084; C10M 2223/045; C10M 141/10; C10M 129/68; C10M 129/72; C10M 129/76; C10M 137/10; C10N 2030/06; C10N 2030/24; C10N 2030/02; C10N 2040/25; C10N 2040/08; C10N 2040/20
See application file for complete search history.

(56) References Cited

U.S. PATENT DOCUMENTS

| 4,010,007 A | * | 3/1977 | Bollinger | ............... | C10L 1/2222 |
| | | | | | 252/392 |
| 10,351,791 B2 | * | 7/2019 | Reid | ....................... | F02M 25/00 |
| 2010/0093573 A1 | * | 4/2010 | Kocsis | ................. | C10M 141/06 |
| | | | | | 508/555 |
| 2020/0277534 A1 | * | 9/2020 | Petts | ..................... | C07C 201/00 |

FOREIGN PATENT DOCUMENTS

| GB | 1548253 A | 7/1979 |
| JP | H1067995 A | 3/1998 |
| JP | 2005002215 A | 1/2005 |
| JP | 2007131792 A | 5/2007 |
| JP | 2008255239 A | 10/2008 |
| JP | 2011214004 A | 10/2011 |
| JP | 4806198 B2 | 11/2011 |
| JP | 2015168813 A | 9/2015 |
| WO | 2018178687 A1 | 10/2018 |

OTHER PUBLICATIONS

International Search Report of PCT Patent Application No. PCT/JP2020/010345 dated May 26, 2020.

* cited by examiner

*Primary Examiner* — Vishal V Vasisth

(57) ABSTRACT

A lubricant additive includes a monoester carboxylic acid salt (A) represented by formula (1).

[Chem. 1]

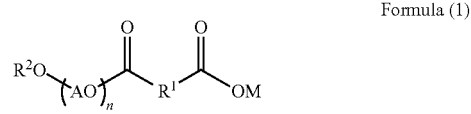

Formula (1)

In formula (1), $R^1$ represents a single bond between carbon atoms of carbonyl groups, or a divalent hydrocarbon group having 1 to 4 carbon atoms, and $R^2$ represents a hydrocarbon group having 1 to 22 carbon atoms. AO represents an oxyalkylene group of one type selected from oxyalkylene groups having 2 to 4 carbon atoms, or a mixed oxyalkylene group of two or more types selected from oxyalkylene groups having 2 to 4 carbon atoms, and n is an average number of added moles of the oxyalkylene group represented by AO and is 0 to 5. M represents organic ammonium.

4 Claims, No Drawings

LUBRICANT ADDITIVE, LUBRICANT ADDITIVE COMPOSITION, AND LUBRICATING OIL COMPOSITION CONTAINING THE SAME

This application is a 371 of PCT/JP2020/010345, filed Mar. 10, 2020.

FIELD

The present invention relates to a lubricant additive, a lubricant additive composition, and a lubricating oil composition containing the lubricant additive or the lubricant additive composition. More specifically, the present invention relates to an ash-free type multifunctional lubricant additive capable of imparting various functions such as wear resistance and metal corrosion resistance to a lubricant base oil (hereinafter, also simply referred to as "base oil") stably over time, the lubricant additive not containing metal components such as zinc, not containing phosphorus and sulfur, and not generating ash components when being used. The present invention also relates to a lubricant additive composition capable of imparting various functions such as load bearing capacity and metal corrosion resistance to a base oil stably over time, and a lubricating oil composition containing the lubricant additive or the lubricant additive composition.

BACKGROUND

Lubricating oils used in engine oil, hydraulic oil, metalworking oil, and the like are composed of a base oil and an additive having various functions. Among the functions of lubricating oils, wear resistance and load bearing capacity are considered as being particularly important, and zinc dithiophosphate (ZnDTP) is generally used as a typical additive for imparting wear resistance and load bearing capacity to lubricating oils.

However, ZnDTP is a compound containing zinc, phosphorus, and sulfur, and ash components are generated by combustion of metal components such as zinc. For example, when ZnDTP is contained in the engine oil of a diesel vehicle, ash components are generated by driving the engine, and these ash components may promote clogging of a diesel particulate filter (DPF) mounted in the diesel vehicle. Further, if phosphorus or sulfur are contained in the engine oil, there may be a stronger influence on a three-way catalyst used to purify exhaust gases of an automobile. Therefore, an ash-free type wear-resistant agent that does not contain metal components such as zinc, does not contain phosphorus and sulfur, and does not generate ash components is desired. For example, as an ash-free type wear-resistant agent, PTL 1 discloses a neutralized salt composed of a monoester carboxylic acid and an aliphatic amine, the monoester carboxylic acid composed of a basic acid and an aliphatic alcohol.

In recent years, with the demand for energy saving, there is a desire to reduce the viscosity of lubricating oils so as to lower the viscous resistance of the lubricating oil. However, if the viscosity of the lubricating oil is reduced, an oil film formed on a friction surface is thin, so that wear is caused by the contact between friction surfaces, and thus, equipment may deteriorate. Therefore, the wear-resistant agent is required to exhibit good lubricity in various temperature and load regions, and further improvement of the compound mentioned above is desired.

In addition to wear resistance, lubricating oils need to have various performance characteristics such as demulsibility and metal corrosion resistance. Therefore, a plurality of additives are generally used together with a wear-resistant agent.

However, in some combinations of additives, there may be incompatibility between additives, and when such a combination is used, these additives may hamper each other's performance. Further, it is desired that the lubricating oil can be used for a long time, and thus, it is required that various functions can be imparted with one type of additive and these functions are stably exhibited for a long time.

For example, PTL 2 discloses, as an ash-free type multifunctional additive, a neutralization product of a condensation reaction mixture for improving metal corrosion resistance, which is obtained by reacting a polyhydric alcohol with a polyprotic carboxylic acid. However, the development of an ash-free type multifunctional additive with further improved stability over time is desired.

On the other hand, if the added amount of ZnDTP is reduced, the load bearing capacity may decrease. Therefore, various studies are conducted to improve the load bearing capacity while reducing the added amount of ZnDTP. For example, PTL 3 discloses a lubricating oil agent containing a combination of a polysulfide extreme pressure agent and ZnDTP and PTL 4 discloses a lubricating oil composition containing a combination of a phosphonate ester and ZnDTP.

With the increase in speed and pressure, and miniaturization of industrial machines in recent years, mechanical elements such as hydraulic machines, compression machines, and bearings are being operated under harsher conditions. Therefore, lubricating oils used in these machines need to exhibit excellent lubricating performance for a long period of time even under high pressure, high load, and high temperature conditions. Further, in addition to load bearing capacity, the lubricating oil is required to have various performance characteristics such as metal corrosion resistance, and further improvement of the lubricant additive is desired.

In these circumstances, PTL 5 discloses an engine oil composition containing a combination of a glycerol fatty acid partial ester and ZnDTP, for example. However, this engine oil composition does not have sufficient load bearing capacity, and the development of a lubricant additive also having further improved stability over time is desired.

CITATION LIST

Patent Literature

PTL 1: Japanese Unexamined Patent Application Publication No. H10-67995 A
PTL 2: Japanese Unexamined Patent Application Publication No. 2015-168813 A
PTL 3: Japanese Patent No. 4806198
PTL 4: Japanese Unexamined Patent Application Publication No. 2005-2215 A
PTL 5: Japanese Unexamined Patent Application Publication No. 2007-131792 A

SUMMARY

Technical Problem

An object of the present invention is to solve the above-described problems, and more specifically, to provide an ash-free type multifunctional lubricant additive capable of imparting various functions such as wear resistance and metal corrosion resistance to a base oil stably over time, the lubricant additive not containing metal components such as zinc, not containing phosphorus and sulfur, and not generating ash components when being used, and also to provide a lubricating oil composition containing the lubricant additive.

Furthermore, another object of the present invention is to provide a lubricant additive composition capable of imparting various functions such as load bearing capacity and metal corrosion resistance to a base oil stably over time, while allowing for a reduction of the added amount of ZnDTP, and to provide a lubricating oil composition containing the lubricant additive composition.

Solution to Problem

As a result of diligent studies in order to achieve the above object, the present inventors have found that, by adding, to a base oil, a neutralized salt of an amine and a monoester carboxylic acid composed of a monoalcohol and a dibasic acid, as a lubricant additive, it is possible to obtain a lubricating oil having excellent functions relating to wear resistance and metal corrosion resistance.

Further, the present inventors have found that, when ZnDTP is added to the base oil in a specific quantitative ratio with respect to the above-mentioned lubricant additive, a lubricating oil having excellent functions relating to load bearing capacity and metal corrosion resistance is obtained, which led to the completion of the present invention. The present invention based on these findings is described in (1) to (4) below.

(1) A lubricant additive including a monoester carboxylic acid salt (A) represented by formula (1).

[Chem. 1]

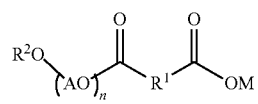

Formula (1)

In formula (1), $R^1$ represents a single bond between carbon atoms of carbonyl groups, or a divalent hydrocarbon group having 1 to 4 carbon atoms, and $R^2$ represents a hydrocarbon group having 1 to 22 carbon atoms. AO represents an oxyalkylene group of one type selected from oxyalkylene groups having 2 to 4 carbon atoms, or a mixed oxyalkylene group of two or more types selected from oxyalkylene groups having 2 to 4 carbon atoms, and n is an average number of added moles of the oxyalkylene group represented by AO and is 0 to 5. M represents organic ammonium.

(2) A lubricant additive composition including the lubricant additive according to (1) above and zinc dithiophosphate (C) represented by formula (2), in which (A):(B) being a mass ratio of the monoester carboxylic acid salt (A) to the zinc dithiophosphate (B) is 99:1 to 1:99.

[Chem. 2]

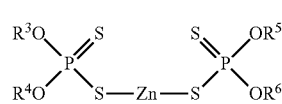

Formula (2)

In formula (2), $R^3$ to $R^6$ each independently represent a hydrocarbon group having 1 to 24 carbon atoms.

(3) A lubricating oil composition including 70 to 99.99 mass % of a lubricant base oil and 0.01 to 30 mass % of the lubricant additive according to (1) above.

(4) A lubricating oil composition including 70 to 99.99 mass % of a lubricant base oil and 0.01 to 30 mass % of the lubricant additive composition according to (2) above.

Advantageous Effects of Invention

A lubricant additive according to the present invention is capable of imparting various functions such as wear resistance and metal corrosion resistance to a lubricant base oil stably over time. Moreover, the lubricant additive according to the present invention is an ash-free type lubricant additive that does not generate ash components when being used, and thus, does not clog a filter such as a DPF, and further, does not contain phosphorus atoms or sulfur atoms, so that the influence on a three-way catalyst is reduced. Therefore, a lubricating oil composition containing the lubricant additive according to the present invention and a lubricant base oil has excellent functions relating to wear resistance and metal corrosion resistance, even if no ZnDTP is added.

The lubricant additive composition according to the present invention is capable of imparting various functions such as load bearing capacity and metal corrosion resistance to a lubricant base oil stably over time, while allowing for a reduction of the added amount of ZnDTP. Therefore, the lubricating oil composition containing the lubricant additive composition according to the present invention and a lubricant base oil is excellent in maintaining functions relating to load bearing capacity and metal corrosion resistance, and allows for a reduction of ash generation.

DESCRIPTION

Below, embodiments of a lubricant additive (hereinafter, also simply referred to as "additive") according to the present invention, a lubricant additive composition (hereinafter, also simply referred to as "additive composition") according to the present invention, and a lubricating oil composition containing the additive or the additive composition and a lubricant base oil will be described in detail.

Note that numerical ranges specified by using the word "to" include numerical values on both sides of the word "to" (an upper limit and a lower limit). For example, "2 to 10" means a range of 2 or more and 10 or less.

Further, when a concentration or an amount is specified, any higher concentration or amount can be associated with any lower concentration or amount. For example, when ranges of "2 to 10 mass %" and "preferably 4 to 8 mass %" are mentioned, this expression also includes ranges such as "2 to 4 mass %", "2 to 8 mass %", "4 to 10 mass %", and "8 to 10 mass %".

Lubricant Additive

The additive according to the present invention is a compound represented by formula (1) below, and this compound is a neutralized salt of an organic amine and a monoester carboxylic acid composed of a monoalcohol and a dibasic acid. Note that the compound represented by formula (1) is also simply referred to as "monoester carboxylic acid salt (A)" hereinafter. One type of the monoester carboxylic acid salt (A) can be used alone or two or more types of the monoester carboxylic acid salt (A) can be used in combination.

[Chem. 1]

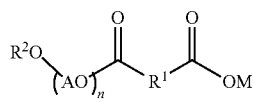

Formula (1)

In formula (1), $R^1$ represents a single bond between carbon atoms of carbonyl groups, or a divalent hydrocarbon group having 1 to 4 carbon atoms. The divalent hydrocarbon group having 1 to 4 carbon atoms is a functional group consisting of a carbon atom and a hydrogen atom, is one type selected from an alkylene group and an alkenylene group, and may be linear or branched. When the hydrocarbon group has 5 or more carbon atoms, the chain length is long, so that sufficient wear resistance and load bearing capacity may not be obtained.

$R^1$ is preferably an alkylene group or an alkenylene group having 2 carbon atoms, specific examples thereof include an ethylene group and an ethenylene group, and the ethylene group is more preferable.

In formula (1), $R^2$ represents a saturated or unsaturated hydrocarbon group having 1 to 22 carbon atoms, and may be linear or branched. Examples of $R^2$ include linear saturated hydrocarbon groups such as a methyl group, an ethyl group, a propyl group, a butyl group, a hexyl group, a heptyl group, an octyl group, a lauryl group, a myristyl group, a palmityl group, a stearyl group, and a behenyl group; branched saturated hydrocarbon groups such as an isopropyl group, an isobutyl group, a t-butyl group, an isopentyl group, an isooctyl group, a 2-ethylhexyl group, an isononyl group, a 3,5,5-trimethylhexyl group, an isodecyl group, an isostearyl group, a 2-octyldecyl group, a 2-octyldodecyl group, and a 2-hexyldecyl group; and unsaturated hydrocarbon groups such as an allyl group, a (meth)acryl group, a palmitoyl group, an oleyl group, and a linoleyl group. One type of compound including these hydrocarbon groups may be used alone, or two or more types of compounds including these hydrocarbon groups may be mixed and used. When the hydrocarbon group has 23 or more carbon atoms, sufficient wear resistance and load bearing capacity may not be obtained.

From the viewpoint of wear resistance and load bearing capacity, $R^2$ is preferably a linear or branched saturated hydrocarbon group or a linear or branched unsaturated hydrocarbon group having 4 to 18 carbon atoms, more preferably, a branched saturated hydrocarbon group or a branched unsaturated hydrocarbon group having 8 to 18 carbon atoms, and even more preferably, a branched unsaturated hydrocarbon group having 16 to 18 carbon atoms. For example, a 2-ethylhexyl group, an isodecyl group, an isostearyl group, and an oleyl group are preferable, and an oleyl group is particularly preferable.

In formula (1), AO is an oxyalkylene group having 2 to 4 carbon atoms, and may be linear or branched. Examples of AO include an oxyethylene group, an oxypropylene group, an oxybutylene group, and an oxytetramethylene group. AO is preferably an oxyalkylene group having 2 to 3 carbon atoms, and more preferably an oxyethylene group having 2 carbon atoms.

n represents the average number of added moles of the oxyalkylene group, and n is 0 to 5. From the viewpoint of wear resistance, load bearing capacity, and stability over time, n is preferably 1 or more. Further, n is preferably 4 or less, and particularly preferably 3 or less. When n is 2 to 5, a plurality of oxyalkylene groups of a single type may be bonded (one type oxyalkylene groups), or a plurality of oxyalkylene groups including two or more types of oxyalkylene groups may be bonded in a mixed manner (mixed oxyalkylene groups).

In formula (1), M represents organic ammonium. Examples of the organic ammonium include primary, secondary, tertiary, and quaternary ammonium cations in which a saturated or unsaturated hydrocarbon group having 1 to 24 carbon atoms is bonded to a nitrogen atom, and these ammonium cations may be linear, branched, or cyclic. Further, hydrocarbon groups in the secondary, tertiary, and quaternary ammonium cations may be the same, or at least one of the hydrocarbon groups may be different. Examples of the organic ammonium include ethylammonium, diethylammonium, dioctylammonium, triethylammonium, trioctylammonium, lauryldimethylammonium, and stearyldimethylammonium. From the viewpoint of metal corrosion resistance and stability over time, tertiary ammonium is preferable.

Relating to the total number of carbon atoms included in the above-mentioned $R^2$, AO, and M (organic ammonium) of formula (1), from the viewpoint of wear resistance and metal corrosion resistance, the value of expression (3) below is preferably 0.5 to 2.0, more preferably 0.6 to 1.8, and particularly preferably 0.7 to 1.5.

[(Total number of carbon atoms in organic ammonium)]/[(number of carbon atoms in $R^2$)+(number of carbon atoms in AO)×$n$]    Expression (3)

Next, a method for producing the monoester carboxylic acid salt (A) represented by formula (1) will be described.

The method for producing the monoester carboxylic acid salt (A) represented by formula (1) is not particularly limited, but the monoester carboxylic acid salt (A) represented by formula (1) can be produced via a first step of producing a monoester carboxylic acid and a second step of neutralizing the monoester carboxylic acid obtained in the first step with an amine compound.

The first step will be described.

An example of the first step includes a method of subjecting a dibasic acid and an alcohol including a hydrocarbon group having 4 to 22 carbon atoms or a polyether compound obtained by adding an alkylene oxide to the alcohol, to an esterification reaction at 60 to 180° C. From the viewpoint of reactivity, it is preferable to use an acid anhydride as the dibasic acid in the esterification reaction for producing the compound. Further, it is preferable to use an equal amount of alcohol in molar ratio with respect to the acid anhydride.

Next, the second step will be described.

The monoester carboxylic acid salt (A) can be produced by subjecting the monoester carboxylic acid produced by the above-described production method and an amine compound to a neutralization reaction at 20 to 60° C., for example. From the viewpoint of wear resistance and load bearing capacity, a molar ratio of the monoester carboxylic acid to the amine compound is preferably in a range from 60:40 to 40:60, more preferably in a range from 55:45 to 45:55, and even more preferably in a range from 52:48 to 48:52.

Lubricant Additive Composition

The additive composition according to the present invention contains the above-described monoester carboxylic acid salt (A) and zinc dithiophosphate (B) described below.

Zinc Dithiophosphate (B)

Zinc dithiophosphate (B) is a compound represented by formula (2) below, and one type of zinc dithiophosphate (B) can be used alone or two or more types of zinc dithiophosphates (B) can be used in combination.

[Chem. 2]

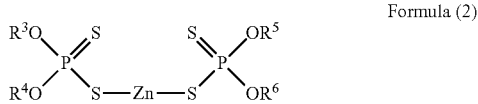

Formula (2)

In formula (2), $R^3$ to $R^6$ each independently represent a hydrocarbon group having 1 to 24 carbon atoms, and $R^3$ to $R^6$ may be the same or may be different from each other. The hydrocarbon group having 1 to 24 carbon atoms is a saturated or unsaturated hydrocarbon group consisting of a carbon atom and a hydrogen atom, and may be linear or branched. Examples of the hydrocarbon group having 1 to 24 carbon atoms include an alkyl group, an alkenyl group, a cycloalkyl group, an aryl group, and an aralkyl group.

$R^3$ to $R^6$ are preferably linear or branched alkyl groups having 3 to 18 carbon atoms, more preferably, linear or branched alkyl groups having 3 to 12 carbon atoms, and even more preferably, branched alkyl groups having 3 to 12 carbon atoms.

Examples of the linear alkyl group having 3 to 12 carbon atoms include a propyl group, a butyl group, a pentyl group, a hexyl group, an octyl group, and a decyl group, and the butyl group and the pentyl group are more preferable. Further, zinc dithiophosphate (C) includes preferably two or more types of the above-mentioned linear alkyl groups as $R^3$ to $R^6$, and it is particularly preferable that zinc dithiophosphate (C) includes both a linear butyl group and a linear pentyl group.

Examples of the branched alkyl group having 3 to 12 carbon atoms include an isopropyl group, an isobutyl group, an isopentyl group, a neopentyl group, an isohexyl group, a 2-ethylhexyl group, a 3,5,5-trimethylhexyl group, and an isodecyl group, and the isohexyl group, the 2-ethylhexyl group, and the 3,5,5-trimethylhexyl group are more preferable, and the isohexyl group is even more preferable.

Typical examples of ZnDTP include LUBRIZOL 677A and LUBRIZOL 1371, which are commercially available from Lubrizol Corporation.

The mixing ratio of the monoester carboxylic acid salt (A) represented by formula (1) and zinc dithiophosphate (B) represented by formula (2) is 99:1 to 1:99 when expressed as a mass ratio, preferably 90:10 to 10:90, more preferably 80:20 to 20:80, and even more preferably 60:40 to 40:60. If the content of the monoester carboxylic acid salt (A) is too high, the load bearing capacity may decrease, and if the content of the monoester carboxylic acid salt (A) is too low, the load bearing capacity may not be stable over time.

The additive composition according to the present invention contains at least the monoester carboxylic acid salt (A) and zinc dithiophosphate (B), and may further contain other additives such as extreme pressure agents, wear-resistant agents, and antioxidants, as long as the effects of the additive composition according to the present invention are not impaired.

Lubricating Oil Composition

The lubricating oil composition according to the present invention contains the additive according to the present invention or the additive composition according to the present invention, and a lubricant base oil. The lubricating oil composition containing the additive according to the present invention and the lubricant base oil is referred to as "lubricating oil composition (1)", and the lubricating oil composition containing the additive composition according to the present invention and the lubricant base oil is referred to as "lubricating oil composition (2)".

Various lubricant base oils can be employed as the lubricant base oil in the present invention. Examples of the lubricant base oil include conventionally used lubricant base oils such as mineral oils, highly refined mineral oils, animal and vegetable oils and fats, synthetic esters, poly-α-olefins, and gas-to-liquid (GTL) oils.

Concerning each of the contents of the lubricant base oil and the additive in the lubricating oil composition (1) of the present invention, the content of the lubrication base oil is 70 to 99.99 mass % and the content of the additive is 0.01 to 30 mass %. The content of the lubrication base oil is preferably 80 to 99.95 mass %, and more preferably 90 to 99.9 mass %. The content of the additive is preferably 0.05 to 20 mass %, and more preferably 0.1 to 10 mass %. If the content of the additive in the lubricating oil composition (1) of the present invention is too small, sufficient wear resistance may not be obtained. Further, if the content of the additive is too large, metal corrosion resistance corresponding to the added amount may not be obtained.

Note that the total of the contents of the lubricant base oil and the additive is 100 mass %.

Concerning each of the contents of the lubricant base oil and the additive composition in the lubricating oil composition (2) of the present invention, the content of the lubrication base oil is 70 to 99.99 mass % and the content of the additive composition is 0.01 to 30 mass %. The content of the lubrication base oil is preferably 80 to 99.95 mass %, and more preferably 90 to 99.9 mass %. The content of the additive composition is preferably 0.05 to 20 mass %, and more preferably 0.1 to 10 mass %. If the content of the additive composition in the lubricating oil composition (2) of the present invention is too small, sufficient load bearing capacity may not be obtained. Further, if the content of the additive composition is too large, load bearing capacity and metal corrosion resistance corresponding to the added amount may not be obtained.

Note that the total of the contents of the lubricant base oil and the additive composition is 100 mass %.

If required, additives such as detergent dispersants, viscosity index improvers, anti-rust agents, corrosion inhibitors, pour point depressants, and metal deactivators may also be added to the lubricating oil compositions (1) and (2) according to the present invention.

The order in which blending, mixing, and addition of the additives are performed is not particularly limited, and various methods can be adopted. For example, in the case of preparing the lubricating oil composition (2) of the present invention, a method may be employed in which the monoester carboxylic acid salt (A), zinc dithiophosphate (B), and optional various types of additives are added to the lubricant base oil and mixed by heating, or a method may be employed in which a solution having a high concentration of each of the additives is prepared in advance and this solution is mixed with the lubricant base oil.

EXAMPLES

Below, the present invention will be described in more detail with reference to examples and comparative examples.

An example of producing the monoester carboxylic acid salt (A) represented by formula (1) is described in Synthesis Example 1 below. Further, an example of preparing the lubricating oil composition (1) containing the monoester carboxylic acid salt (A) is described in Formulation Example 1 below.

Synthesis Example 1, Compound (A-1) of Formula (1)

1070 g (4 mol) of oleyl alcohol and 1.3 g of potassium hydroxide were introduced into a stainless steel 5 liter pressure-resistant container equipped with a stirrer, a pressure gauge, a thermometer, a safety valve, a gas blowing pipe, an exhaust pipe, a cooling coil, and a steam jacket, and after a nitrogen purge, the mixture was heated to 120° C. while being stirred. While the mixture was stirred, 180 g (4 mol) of ethylene oxide was added from a separately prepared pressure-resistant container through the gas blowing pipe while applying pressure with nitrogen gas, under conditions of 120° C. and 0.05 to 0.50 MPa (gauge pressure). After ethylene oxide was completely added, the mixture was allowed to react under the same conditions until the internal pressure was constant. Subsequently, the reaction product was taken out of the pressure-resistant container and neutralized with hydrochloric acid to pH 6-7. In order to remove water contained in the reaction product, the reaction product was subjected to a reduced pressure treatment at 100° C. for 1 hour. Finally, salt was removed by filtration to obtain 1200 g of a polyether compound. The hydroxyl value of the obtained polyether compound was 180, and the molecular mass calculated based on the hydroxyl value was 312.

Next, 312 g (1 mol) of the polyether compound obtained as described above and 100 g (1 mol) of succinic anhydride were introduced into a 1-liter glass reaction vessel equipped with a stirring device, a thermometer, and a nitrogen introduction tube, and the mixture was allowed to react at 100° C. for 2 hours. After measuring the acid number to confirm that 99% or more of the acid anhydride was half-esterified, the mixture was cooled to room temperature. Subsequently, 213 g (1 mol) of lauryldimethylamine was introduced into the reaction vessel and the mixture was stirred and neutralized at 60° C. or less for 0.5 hours. Thereby, compound (A-1) was obtained.

Compounds (A-2) to (A-7) of formula (1) shown in Table 1 were synthesized by using other compounds instead of oleyl alcohol, ethylene oxide, succinic anhydride, and lauryldimethylamine in Synthesis Example 1, as appropriate, and performing operation according to Synthesis Example 1. These compounds (A-2) to (A-7) were used as lubricant additives to prepare lubricating oil compositions (1-1) to (1-7), as described in Formulation Example 1.

Table 1 shows a relationship between the compounds (A-1) to (A-7) and the symbols in formula (1), together with the values of Expression (3) mentioned above.

TABLE 1

| Compound | $R^1$ | $R^2$ | AO | n | M | Value of Expression (3) |
|---|---|---|---|---|---|---|
| A-1 | Ethylene | Oleyl | Oxyethylene | 1 | Dimethyllaurylammonium | 0.70 |
| A-2 | Ethylene | Isostearyl | Oxyethylene | 1 | Dimethylstearylammonium | 1.00 |
| A-3 | Ethylene | 2-ethylhexyl | Oxyethylene | 1 | Dimethyllaurylammonium | 1.40 |
| A-4 | Ethylene | 2-ethylhexyl | Oxypropylene | 1 | Dimethyllaurylammonium | 1.70 |
| A-5 | Ethylene | Butyl | Oxyethylene | 2 | Dioctylamine salt | 2.00 |
| A-6 | Ethylene | Isostearyl | Oxyethylene | 1 | Hydrogen atom | 0 |
| A-7 | Ethylene | Oleyl | Oxyethylene | 7 | Dimethyllaurylammonium | 0.44 |

Formulation Example 1, Preparation of Lubricating Oil Composition (1)

0.5 mass % of each of compounds (A-1) to (A-7) mentioned above was blended to a lubricant base oil (poly-α-olefin, kinematic viscosity (40° C.): about 50 mm$^2$/s) to obtain the lubricating oil compositions (1-1) to (1-7) of Examples (1-1) to (1-5) and Comparative Examples (1-1) and (1-2). The obtained lubricating oil compositions (test oils) were subjected to the evaluation tests described below. The evaluation results of Examples (1-1) to (1-5) are shown in Table 2 below, and the evaluation results of Comparative Examples (1-1) and (1-2) are shown in Table 3 below.

Wear Resistance Test

The wear resistance was evaluated by using an SRV test instrument (Schwingungs Reihungundund Verschleiss test instrument type 4, manufactured by OPTIMOL). The SRV test was performed with a ball/disc, and each test piece was made of SUJ-2. The test conditions were a test temperature of 150° C., a load of 100 N, an amplitude of 1 mm, and a frequency of 50 Hz, and the wear scar diameter was measured after a test time of 25 minutes had elapsed.

The evaluation results were assessed as good: wear scar diameter of less than 350 μm, acceptable: 350 μm or more and less than 400 μm, and unacceptable: 400 μm or more.

Further, 100 ml of the test oil was placed into a 100 ml glass bottle and the glass bottle was sealed in an air atmosphere and allowed to stand in a constant temperature bath at 80° C. for 3 days. After that, the wear resistance of the lubricating oil compositions (1-1) to (1-7) was evaluated under the same conditions as described above.

Metal Corrosion Resistance Test

The copper corrosion resistance was evaluated as the metal corrosion resistance. A copper wire cut to a length of 4 cm was polished with a P150 polishing cloth. 2 ml of test oil was placed into a 5 ml screw cap tube, the copper wire was immersed therein, and the tube was heated at 100° C. for 3 hours. The state of the surface of the copper wire before and after the test was compared to evaluate whether corrosion had occurred.

The evaluation results were assessed as good: no corrosion occurred and unacceptable: corrosion occurred.

Further, 100 ml of the test oil was placed into a 100 mL glass bottle and a copper wire was immersed therein. The glass bottle was sealed in an air atmosphere and allowed to stand in a constant temperature bath at 80° C. for 3 days. After that, the metal corrosion resistance of the lubricating oil compositions (1-1) to (1-7) was evaluated under the same conditions as described above.

good wear resistance and metal corrosion resistance after aging, compound (A-7) was inferior in wear resistance immediately after production.

Next, an example of preparing an additive composition containing the compounds (A-1), (A-5), (A-6), and (A-7) of formula (1) shown in Table 1 and zinc dithiophosphate (B) described below is described in Formulation Example 2

TABLE 2

| | | | Examples | | | | |
|---|---|---|---|---|---|---|---|
| | | | 1-1 | 1-2 | 1-3 | 1-4 | 1-5 |
| | | | | Additives (compounds) | | | |
| | | | A-1 | A-2 | A-3 | A-4 | A-5 |
| | | | | Lubricating oil composition (1) | | | |
| | | | 1-1 | 1-2 | 1-3 | 1-4 | 1-5 |
| Abrasion resistance | Wear scar diameter (□m) | Immediately after preparation | Good (320) | Good (335) | Good (345) | Acceptable (360) | Acceptable (365) |
| | | after 3 days at 80° C. | Good (330) | Good (345) | Acceptable (350) | Acceptable (375) | Acceptable (385) |
| Metal corrosion resistance | | Immediately after preparation | Good | Good | Good | Good | Good |
| | | After 3 days at 80° C. | Good | Good | Good | Good | Good |

TABLE 3

| | | | Comparative Examples | |
|---|---|---|---|---|
| | | | 1-1 | 1-2 |
| | | | Additives (compounds) | |
| | | | A-6 | A-7 |
| | | | Lubricating oil composition (1) | |
| | | | 1-6 | 1-7 |
| Abrasion resistance | Wear scar diameter (□m) | Immediately after preparation | Good (340) | Unacceptable (480) |
| | | After 3 days at 80° C. | Acceptable (370) | Unacceptable (490) |
| Metal corrosion resistance | | Immediately after preparation | Good | Good |
| | | After 3 days at 80° C. | Unacceptable | Good |

As can be clearly understood from the results shown in Table 2, the compounds (A-1) to (A-5) related to the additives of the present invention are capable of imparting excellent wear resistance and metal corrosion resistance to a lubricant base oil stably over time. Further, the compounds (A-1) to (A-5) do not contain metal components such as zinc, and thus, the lubricating oil compositions (1-1) to (1-5) of Examples (1-1) to (1-5) containing these compounds (A-1) to (A-5) do not generate ash components when being used, so that filters such as DPF are less likely to be clogged. Further, the compounds (A-1) to (A-5) do not contain phosphorus atoms or sulfur atoms, so that the influence on a three-way catalyst from using the lubricating oil compositions (1-1) to (1-5) of Examples (1-1) to (1-5) is reduced.

On the other hand, as shown in Table 3, although compound (A-6) in which M in formula (1) is outside the range specified in the present invention had good wear resistance, compound (A-6) was inferior in the wear resistance and the metal corrosion resistance after aging.

Further, although compound (A-7) in which n in formula (1) is outside the range specified in the present invention had below. Further, an example of preparing the lubricating oil composition (2) containing the additive composition prepared in Formulation Example 2 is described in Formulation Example 3 below.

Zinc Dithiophosphate: Compounds (B-1) and (B-2) of Formula (2)

LUBRIZOL 677A (alkyl group: branched hexyl group) and LUBRIZOL 1395 (alkyl groups: linear butyl group and linear pentyl group) manufactured by Lubrizol Corp. were used as zinc dithiophosphate. Compound (B-1) is LUBRIZOL 677A and compound (B-2) is LUBRIZOL 1395.

Table 4 shows a relationship between the symbols in formula (2) and the compounds.

TABLE 4

| Compound | $R^3$ to $R^6$ |
|---|---|
| B-1 | Isohexyl group |
| B-2 | Linear butyl group and linear pentyl group |

Formulation Example 2, Preparation of Additive Compositions

A thermometer and a nitrogen introduction tube were inserted into a four-neck flask (300 mL to 1 L), and the additives shown in Table 5 were stirred and mixed at 25° C. for 1 hour to obtain additive compositions 1 to 8.

TABLE 5

| Additive composition | Blending ratio (mass ratio) | | | | | | (A):(B) (mass ratio) |
|---|---|---|---|---|---|---|---|
| | Compound (A) | | | | Compound (B) | | |
| | A-1 | A-5 | A-6 | A-7 | B-1 | B-2 | |
| 1 | 50 | — | — | — | 50 | — | 50:50 |
| 2 | 70 | — | — | — | 30 | — | 70:30 |
| 3 | 15 | — | — | — | 85 | — | 15:85 |
| 4 | — | 50 | — | — | 50 | — | 50:50 |
| 5 | — | 50 | — | — | — | 50 | 50:50 |
| 6 | — | — | 50 | — | 50 | — | 50:50 |
| 7 | — | — | — | 70 | 30 | — | 70:30 |
| 8 | — | — | — | — | 100 | — | 0:100 |

Formulation Example 3, Preparation of Lubricating Oil Composition (2)

0.5 mass % of each of the additive compositions 1 to 8 mentioned in Table 5 above was blended to the lubricant base oil (poly-α-olefin, kinematic viscosity (40° C.): about 50 mm$^2$/s) to obtain the lubricating oil compositions of Examples (2-1) to (2-5) and Comparative Examples (2-1) to (2-3). The obtained lubricating oil composition (2) (test oil) was subjected to the evaluation tests described below. The evaluation results are shown in Tables 6 and 7.

Load Bearing Capacity Test

The seizure load was evaluated with a Shell four-ball tester. The test piece was made of SUJ-2. The test conditions were a test temperature of 25° C., a rotation speed of 1800 rpm, and a test time of 10 seconds, and loads of 50 kg, 63 kg, 80 kg, 100 kg, 126 kg, 160 kg, and 200 kg were applied in this order. In the test, a load at which phenomena such as a sudden increase in friction torque and generation of abnormal noise occurred, and seizure marks were generated on the abrasion surface was defined as the seizure load.

The evaluation results were assessed as good: seizure load of 160 kg or more, acceptable: 126 kg or more and less than 160 kg, and unacceptable: less than 126 kg.

Further, 100 ml of the test oil was placed into a 100 ml glass bottle, the glass bottle was sealed in an air atmosphere and allowed to stand in a constant temperature bath at 80° C. for 3 days. After that, the load bearing capacity of the lubricating oil composition (2) (test oil) was evaluated under the same conditions as described above.

Metal Corrosion Resistance Test

The copper corrosion resistance was evaluated as the metal corrosion resistance. A copper wire cut to a length of 4 cm was polished with a P150 polishing cloth. 2 ml of test oil was placed into a 5 ml screw cap tube, the copper wire was immersed therein, and the tube was heated at 100° C. for 3 hours. The state of the surface of the copper wire before and after the test was compared to evaluate whether corrosion had occurred.

The evaluation results were assessed as good: no corrosion occurred and unacceptable: corrosion occurred.

Further, 100 ml of the test oil was placed into a 100 mL glass bottle and the copper wire was immersed therein. The glass bottle was sealed in an air atmosphere and allowed to stand in a constant temperature bath at 80° C. for 3 days. After that, the metal corrosion resistance of the lubricating oil composition (2) (test oil) was evaluated under the same conditions as described above.

TABLE 6

| | | | Lubricating oil composition (2): Examples | | | | |
|---|---|---|---|---|---|---|---|
| | | | 2-1 | 2-2 | 2-3 | 2-4 | 2-5 |
| | | | Additive composition | | | | |
| | | | 1 | 2 | 3 | 4 | 5 |
| Load bearing capacity | Seizure load (kg) | Immediately after preparation | Good (200) | Good (200) | Good (160) | Good (160) | Acceptable (126) |
| | | After 3 days at 80° C. | Good (200) | Good (160) | Good (160) | Acceptable (126) | Acceptable (126) |
| Metal corrosion resistance | | Immediately after preparation | Good | Good | Good | Good | Good |
| | | After 3 days at 80° C. | Good | Good | Good | Good | Good |

TABLE 7

| | | | Lubricating oil composition (2): Comparative Examples | | |
|---|---|---|---|---|---|
| | | | 2-1 | 2-2 | 2-3 |
| | | | Additive composition | | |
| | | | 6 | 7 | 8 |
| Load bearing capacity | Seizure load (kg) | Immediately after preparation | Good (200) | Unacceptable (80) | Unacceptable (100) |
| | | After 3 days at 80° C. | Unacceptable (100) | Unacceptable (80) | Unacceptable (100) |
| Metal corrosion resistance | | Immediately after preparation | Good | Good | Good |
| | | After 3 days at 80° C. | Unacceptable | Good | Good |

As can be clearly understood from the results shown in Table 6, the lubricating oil compositions (2) of Examples (2-1) to (2-5) using the additive compositions 1 to 5 according to the present invention exhibited excellent load bearing capacity and metal corrosion resistance stably over time. That is, the additive compositions 1 to 5 can impart load bearing capacity and metal corrosion resistance to a base oil, and also have excellent characteristics in maintaining these functions. Further, in the additive compositions 1 to 5, it is possible to reduce the blending amount of zinc dithiophosphate (B) with respect to the lubricant base oil (PAO), so that the generation of ash components can be reduced.

On the other hand, concerning Comparative Example (2-1) using the additive composition 6 containing compound (A-6) in which M in formula (1) is outside the range specified in the present invention, the lubricating oil composition (test oil) had good load bearing capacity and metal corrosion resistance immediately after preparation, but was inferior in the stability (durability) of the load bearing capacity and the metal corrosion resistance over time.

Further, Comparative Example (2-2) using the additive composition 7 containing compound (A-7) in which n in formula (1) is outside the range specified in the present invention, and Comparative Example (2-3) using the additive composition 8 consisting only of zinc dithiophosphate (B) had good metal corrosion resistance and were also good in durability of the metal corrosion resistance, but was already inferior in the load bearing capacity at the time immediately after preparation.

RELATED APPLICATIONS

The present application claims priority on the basis of Japanese Patent Application filed on Mar. 14, 2019 (Japanese Patent Application No. 2019-047823) and Japanese Patent Application filed on Feb. 20, 2020 (Japanese Patent Application No. 2020-027132), the entire contents of which are incorporated herein by reference.

What is claimed is:

1. A lubricant additive, comprising:
a monoester carboxylic acid salt (A) represented by formula (1),

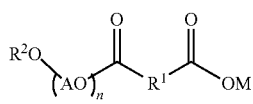

Formula (1)

wherein $R^1$ represents a divalent hydrocarbon group having 2 carbon atoms, $R^2$ represents a linear or branched saturated hydrocarbon group or a linear or branched unsaturated hydrocarbon group having 4 to 18 carbon atoms, AO represents an oxyalkylene group of one type selected from oxyalkylene groups having 2 to 3 carbon atoms, or a mixed oxyalkylene group of two or more types selected from oxyalkylene groups having 2 to 3 carbon atoms, n is an average number of added moles of the oxyalkylene group represented by AO and is 1 to 3, and M represents organic ammonium selected from the group of secondary and tertiary ammonium cations in which a saturated or unsaturated hydrocarbon group having 1 to 24 carbon atoms is bonded to a nitrogen atom.

2. A lubricant additive composition, comprising:
the lubricant additive according to claim 1; and
zinc dithiophosphate (B) represented by formula (2),

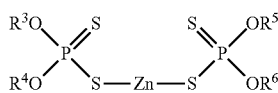

Formula (2)

wherein $R^3$ to $R^6$ each independently represents a hydrocarbon group having 1 to 24 carbon atoms, wherein (A):(B) being a mass ratio of the monoester carboxylic acid salt (A) to the zinc dithiophosphate (B) is 99:1 to 1:99.

3. A lubricating oil composition, comprising:
90 to 99.9 mass% of a lubricant base oil; and
0.1 to 10 mass% of the lubricant additive according to claim 1.

4. A lubricating oil composition, comprising:
70 to 99.99 mass% of a lubricant base oil; and
0.01 to 30 mass% of the lubricant additive composition according to claim 2.

* * * * *